United States Patent
Shelchuk et al.

(10) Patent No.: US 7,181,277 B1
(45) Date of Patent: Feb. 20, 2007

(54) METHODS AND SYSTEMS FOR REDUCING THE LIKELIHOOD OF ARRHYTHMIA ONSET

(75) Inventors: Anne M. Shelchuk, San Rafael, CA (US); Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 653 days.

(21) Appl. No.: 10/386,729

(22) Filed: Mar. 11, 2003

(51) Int. Cl.
*A61N 1/00* (2006.01)
*A61B 5/04* (2006.01)

(52) U.S. Cl. .................. 607/9; 607/14; 607/4; 607/59; 600/515; 600/518

(58) Field of Classification Search .................. 607/9, 607/4, 14, 59, 2, 15, 25; 600/515, 518
See application file for complete search history.

(56) References Cited

U.S. PATENT DOCUMENTS

| | | | |
|---|---|---|---|
| 5,480,413 A * | 1/1996 | Greenhut et al. | 607/14 |
| 6,058,328 A * | 5/2000 | Levine et al. | 607/14 |
| 6,487,442 B1 | 11/2002 | Wood | 600/515 |
| 7,062,325 B1 * | 6/2006 | Krig et al. | 607/14 |

OTHER PUBLICATIONS

Andreas Voss et al., "*Postextrasystolic Regulation Patterns of Blood Pressure and Heart Rate in Patients with Idiopathic Dilated Cardiomyopathy*," Journal of Physiology (2002) 538.1, pp. 271-278.

Georg Schmidt et al., "*Heart-Rate Turbulence After Ventricular Premature Beats as a Predictor of Mortality After Acute Myocardial Infarction*," The Lancet, vol. 353 (Apr. 24, 1999), pp. 1390-1396.

Wolfram Grimm et al., "*Prediction of Major Arrhythmia Events and Sudden Cardiac Death in Dilated Cardiomyopathy*," The Marburg Cardiomyopathy Study Design and Description of Baseline Clinical 6Characteristics (Herz Urban & Vogel)(2000). No. 3, pp. 189-199.

Ralf Mrowka et al., "*Blunted Arterial Baroreflex Causes "Pathological" Heart Rate Turbulence*," Am J Physiol Regulatory Integrative Comp Physiol, The American Physiological Society, (2000). pp. R1171-R1175.

D.C. Lin et al., "*Modeling Heart Rate Variability in Healthy Humans: A Turbulence Analogy*," Physical Review Letters, The American Physical Society, vol. 86, No. 8 (2001), pp. 1650-1653.

L. Ceri Davies et al., "*Relation of Heart Rate and Blood Pressure Turbulence Following Premature Ventricular Complexes to Baroreflex Sensitivity in Chronic Congestive Heart Failure*," The American Journal of Cardiology, vol. 87 (Mar. 15, 2001), pp. 737-742.

Xu Zheng et al., "*Primary Study on Heart Rate Variability of Non-Linear Dynamics in Patients with Coronary Artery Disease and Diabetes*," J Biomed Eng 2001.18(2), pp. 316-319.

* cited by examiner

*Primary Examiner*—Robert E. Pezzuto
*Assistant Examiner*—Natasha Patel

(57) ABSTRACT

Various embodiments are directed to providing systems and methods that can reduce the likelihood of arrhythmia onset by effecting a treatment, responsive to a detected premature event, that mimics or otherwise attempts to emulate a healthy heart's natural recovery process. In one particular embodiment, the premature event comprises a premature ventricular contraction or "PVC", and the treatment comprises pacing the patient to mimic or otherwise emulate a turbulence pattern that is typically exhibited by a healthy heart when the heart attempts to recover from the PVC.

20 Claims, 8 Drawing Sheets

METHODS AND SYSTEMS FOR REDUCING THE LIKELIHOOD OF ARRHYTHMIA ONSET

TECHNICAL FIELD

The present invention generally relates to methods and systems for reducing the likelihood of arrhythmia onset.

BACKGROUND

As implantable cardiac stimulation device technology continues to evolve, there is a push to improve and refine the various processes by which such devices collect, process, and use information associated with a patient to effectuate a treatment that best accommodates the individual patient's needs, health and safety.

Cardiac stimulation devices are used to treat a wide variety of cardiac arrhythmias. Cardiac arrhythmias can generally be thought of as disturbances of the normal rhythm of the heart muscle. Cardiac arrhythmias are broadly divided into two major categories, bradyarrhythmia and tachyarrhythmia. Tachyarrhythmia can be broadly defined as an abnormally rapid heart (e.g., over 100 beats/minute, at rest), and bradyarrhythmia can be broadly defined as an abnormally slow heart (e.g., less than 50 beats/minute). Tachyarrhythmias are further subdivided into two major subcategories, namely, tachycardia and fibrillation. Tachycardia is a condition in which the electrical activity and rhythms of the heart are rapid, but organized. Fibrillation is a condition in which the electrical activity and rhythm of the heart are rapid, chaotic, and disorganized. Tachycardia and fibrillation are further classified according to their location within the heart, namely, either atrial or ventricular.

In general, atrial arrhythmias are non-life threatening, chronic conditions, because the atria (upper chambers of the heart) are only responsible for aiding the movement of blood into the ventricles (lower chambers of the heart), whereas ventricular arrhythmias are life-threatening, acute events, because the heart's ability to pump blood to the rest of the body is impaired if the ventricles become arrhythmic.

Various arrhythmias can be brought on by, or their likelihood of occurrence can be increased in some individuals by so-called "premature events." Examples of premature events include premature atrial contractions (PACs) and premature ventricular contractions (PVCs) also termed "premature beats". Premature beats or contractions are beats that occur earlier than expected and briefly interrupt the normal heart rhythm. Premature beats are the most common cause of an irregular heartbeat. Although they tend to be more common in people with heart disease, almost everyone experiences them at least occasionally. Premature beats often cause a sensation of a "skipped beat" or "flip-flop." What are really felt are not the premature beats themselves but rather the forceful beat that follows the pause after the premature beat. During the pause, the heart has more time to fill with blood making the next beat more forceful. Premature beats are sometimes, but not always, associated with other arrhythmias.

Premature beats may originate from anywhere in the heart. The most common forms of premature beats seen in daily practice are premature contractions originating in the ventricle (PVC) and premature contractions in the atria (PAC).

The presence of premature beats usually is not a major concern. Premature contractions are common in normal individuals. Their presence alone does not require treatment unless they cause intolerable symptoms. Very often, a few changes in lifestyle, such as reducing stress or avoiding caffeine, will be sufficient to regulate the heartbeat. If premature ventricular beats are frequent or occur in certain patterns, they may be indicative of more serious problems.

Because of the increased likelihood of arrhythmias in some individuals who experience premature events such as PVCs and PACs, it can be desirable to treat or administer therapy when such premature events are detected.

One type of treatment or therapy that has developed is rate smoothing therapy. For example, patients typically have a characteristic RR interval. The RR interval is the distance between two successive R-waves, where an R-wave is associated with a patient's heart beat. When a person experiences a PVC, there is typically a compensatory period in which the heart attempts to recover. Some believe that the compensatory period is an attempt by the body's autonomic nervous system to respond to the PVC abnormality.

In many patients who experience an arrhythmia following a PVC, it has been observed that the RR intervals have a characteristic short-long-short pattern. To attempt to avoid PVC-induced or related arrhythmias, various rate smoothing algorithms have been developed to reduce or eliminate the compensatory period and short-long-short pattern. Specifically, these algorithms typically attempt to return a patient to their baseline RR interval as soon as possible. This approach, however, has been observed by some in the field as lacking efficacy in arrhythmia prevention.

Accordingly, this invention arose out of concerns associated with providing improved methods and systems for reducing the likelihood of arrhythmia onset.

SUMMARY

Various embodiments are directed to providing systems and methods that can reduce the likelihood of arrhythmia onset by effecting a treatment, responsive to a detected premature event, that mimics or otherwise attempts to emulate a healthy heart's natural recovery process. In one particular embodiment, the premature event comprises a premature ventricular contraction or "PVC", and the treatment comprises pacing the patient to mimic or otherwise emulate a turbulence pattern that is typically exhibited by a healthy heart when the heart attempts to recover from the PVC.

BRIEF DESCRIPTION OF THE DRAWINGS

Further features and advantages of the claimed embodiments can be more readily understood by reference to the following description taken in conjunction with the accompanying drawings, in which:

DETAILED DESCRIPTION

The following description is of the best mode presently contemplated for practicing the described embodiments. This description is not to be taken in a limiting sense, but rather is made merely for the purpose of describing the general principles of the inventive embodiments. The scope of the described embodiments should be ascertained with reference to the issued claims. In the description of the embodiments that follow, like numerals or reference designators will be used to refer to like parts or elements throughout.

Overview

The various embodiments described below are directed to reducing the likelihood of arrhythmia onset by effecting a treatment, responsive to a detected premature event, that mimics or otherwise attempts to emulate a healthy heart's natural recovery process. By mimicking or emulating a healthy heart's natural recovery process, it is believed that those conditions that lead to various arrhythmias can be avoided as well, thus reducing the likelihood of a patient experiencing an arrhythmia.

As noted above, premature events can occur both in the atria and ventricles. In the example that is used throughout this document, a ventricular premature event in the form of a premature ventricular contraction or PVC is used. It is to be appreciated, however, that the techniques and teachings in this document may have applicability in the atria as well.

Exemplary Stimulation Device

The techniques that are described above and below are intended to be implemented in connection with an implantable cardiac stimulation device that is configured or configurable to stimulate or shock a patient's heart.

Figure 1:
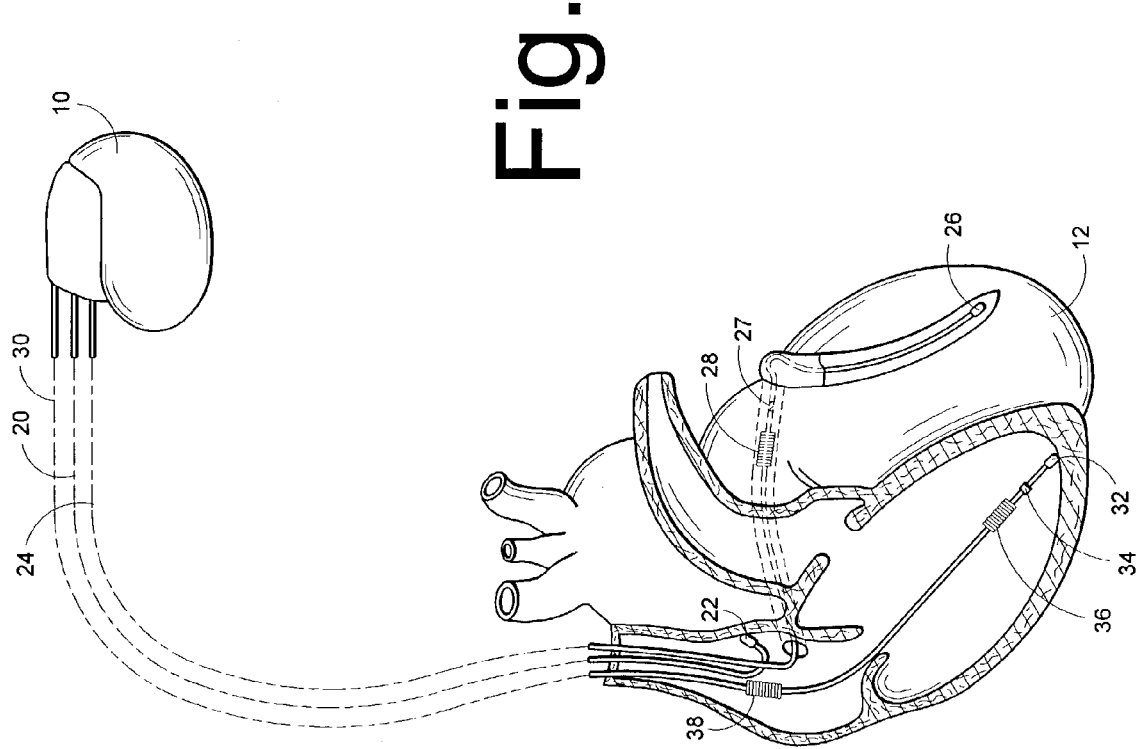
FIG. 1 is a simplified diagram illustrating an implantable stimulation device in electrical communication with leads implanted into a patient's heart for delivering multi-chamber stimulation and shock therapy.

FIG. 1 shows an exemplary stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

Stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
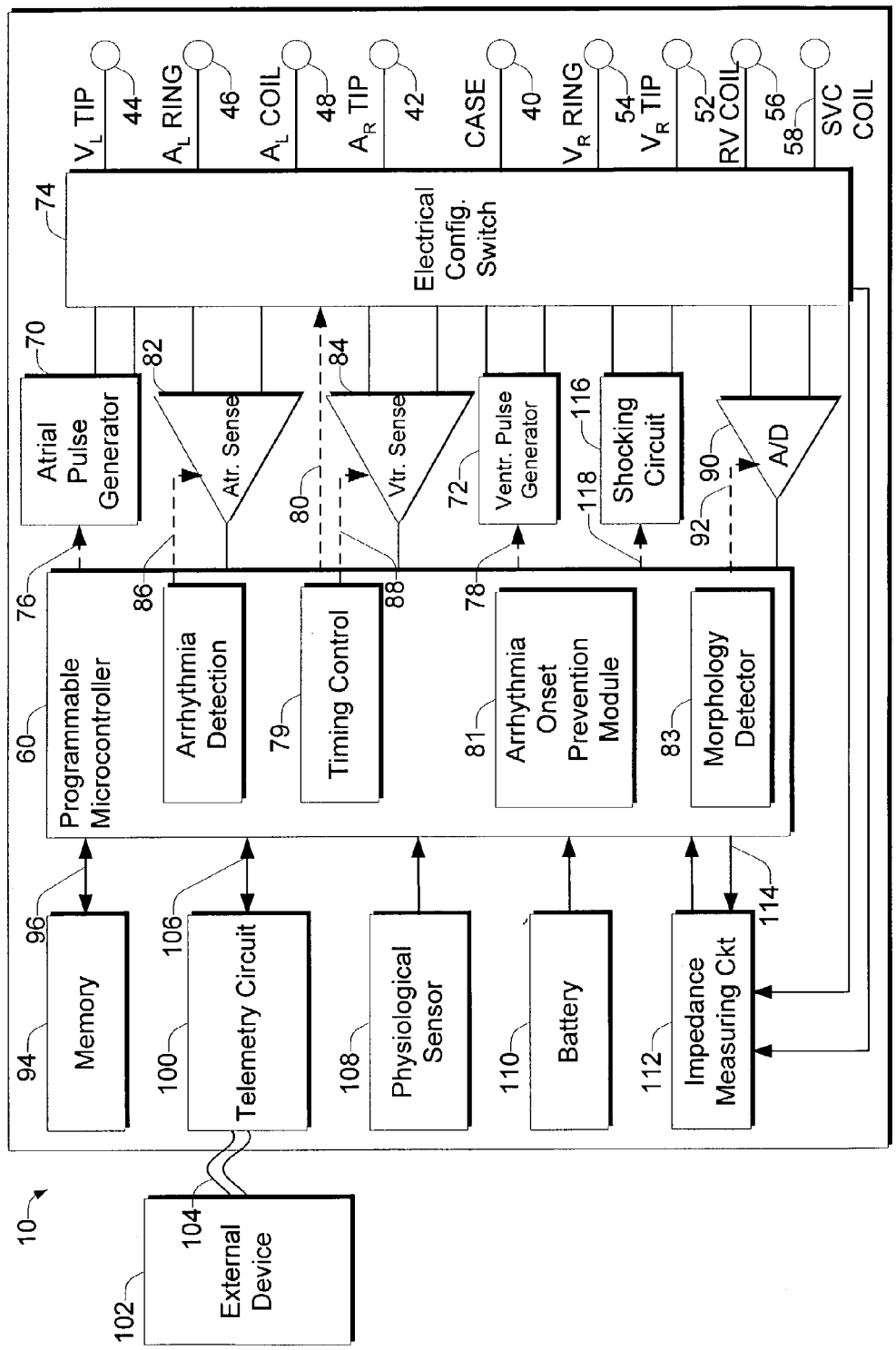
FIG. 2 is a functional block diagram of a multi-chamber implantable stimulation device illustrating the basic elements of a stimulation device which can provide cardioversion, defibrillation and pacing stimulation in four chambers of the heart.

FIG. 2 shows an exemplary, simplified block diagram depicting various components of stimulation device 10. The stimulation device can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the inventive techniques and methods described below can be implemented in connection with any suitably configured or configurable stimulation device. Accordingly, one of skill in the art could readily duplicate, eliminate or disable the appropriate circuitry in any desired combination to provide a device capable of treating the appropriate chamber(s) with cardioversion, defibrillation and pacing stimulation.

Housing 40 for stimulation device 10 is often referred to as the "can", "case" or "case electrode", and may be programmably selected to act as the return electrode for all "unipolar" modes. Housing 40 may further be used as a return electrode alone or in combination with one or more of the coil electrodes 28, 36 and 38, for shocking purposes. Housing 40 further includes a connector (not shown) having a plurality of terminals 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal (RV COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design and operation of the microcontroller 60 are not critical to the described embodiments. Rather, any suitable microcontroller 60 may be used that carries out the functions described herein. The use of microprocessor-based control circuits for performing timing and data analysis functions are well known in the art.

FIG. 2 also shows an atrial pulse generator 70 and a ventricular pulse generator 72 which generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

Microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

Microcontroller 60 can further include an arrhythmia onset prevention module 81 that can be utilized by the stimulation device 10 for administering therapy that is directed to reducing the likelihood of the occurrence of an arrhythmia. Various functionalities associated with this module are discussed below in more detail. In addition, the microcontroller can comprise a morphology detector 83 that is configured to execute dynamic template-matching and compare real-time EGM complexes with a stored template or templates.

A switch 74 includes a plurality of switches for connecting the desired electrodes to the appropriate I/O circuits, thereby providing complete electrode programmability. Accordingly, switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. Switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation.

The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection may occur on a beat-by-beat basis or on a sampled basis. A capture threshold search can desirably be performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. One feature of the described embodiments is the ability to sense and store a relatively large amount of data (e.g., from the data acquisition system 90), which data may then be used for subsequent analysis to guide the programming of the device.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

The stimulation device 10 can further include a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors which sense or enable detection of the oxygen content of blood, respiration rate and/or minute ventilation, pH of blood, ventricular gradient, etc.

The stimulation device additionally includes a battery 110 that provides operating power to all of the circuits shown in FIG. 2. For the stimulation device 10, which employs shocking therapy, the battery 110 is capable of operating at low current drains for long periods of time (e.g. preferably less than 10 μA), and is capable of providing high-current pulses (for capacitor charging) when the patient requires a shock pulse (e.g. preferably, in excess of 2 A, at voltages above 2 V, for periods of 10 milliseconds or more). The battery 110 also desirably has a predictable discharge characteristic so that elective replacement time can be detected. Accordingly, the device 10 preferably employs a power source sufficient to deliver the high voltage shock therapy. One such example is the lithium/silver vanadium oxide battery, as is true for most (if not all) current devices capable of delivering high voltage therapy.

The stimulation device 10 can further include magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

FIG. 2 also shows an impedance measuring circuit 112 which is enabled by the microcontroller 60 via a control signal 114. The known uses for an impedance measuring circuit 120 include, but are not limited to, lead impedance surveillance during the acute and chronic phases for mechanical integrity of the lead, measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used.

In the case where the stimulation device 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of an organized tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of ventricular fibrillation which is a very disorganized rapid ventricular arrhythmia. Accordingly, the microcontroller 60 is capable of controlling the synchronous or asynchronous delivery of the shocking pulses.

Exemplary Embodiment Overview

Figure 3:
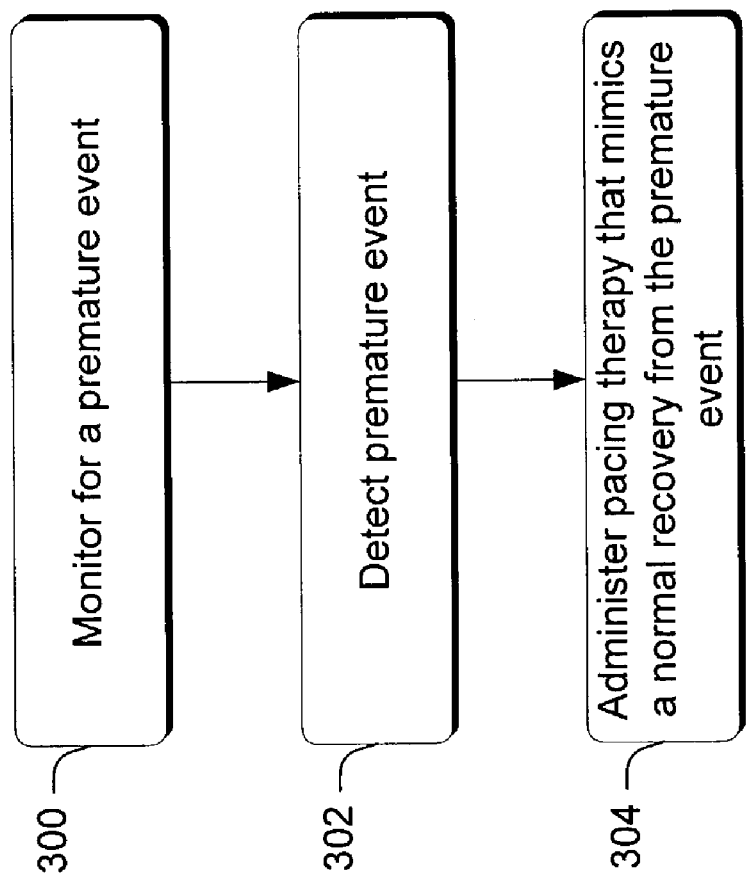
FIG. 3 is a flow diagram that describes steps in a method in accordance with one embodiment.

FIG. 3 is a flow diagram that describes steps in a method in accordance with one embodiment. The steps can be implemented in connection with any suitable hardware, software, firmware or combination thereof. In but one embodiment, the steps can be implemented by a suitably programmed implantable stimulation device. But one example of a stimulation device is given above in FIGS. 1 and 2. It should also be noted that the methods described throughout this document can be embodied as computer-readable instructions that are resident on a computer-readable medium such as a magnetic or optical disk, random access memory (RAM), read only memory (ROM) and the like.

Step 300 monitors for a premature event. The premature event can be any suitable premature event. For example, premature events can comprise atrial or ventricular premature events. Examples of atrial or ventricular premature events include, respectively, premature atrial contractions (PACs) and premature ventricular contractions (PVCs). Step 302 detects a premature event. This step can be implemented using any suitable detection algorithm. Responsive to detecting the premature event, step 304 administers pacing therapy that mimics a normal recovery from the premature event. This step can be implemented by administering one or more pacing pulses that are configured to mimic a normal (or healthy) recovery from the detected premature event. The "normal" recovery can be patient-specific in the sense that the therapy can be tailored to mimic a specific patient's normal recovery from the detected event. Alternately or additionally, the normal recovery can be more generalized in the sense that the therapy represents what is normally expected to be a recovery from such an event.

Treatment Using Different Pacing Rates

As noted above in FIG. 3, detection and treatment of premature events can take place relative to different types of premature events. One such premature event is a premature ventricular contraction or PVC.

Figure 4:
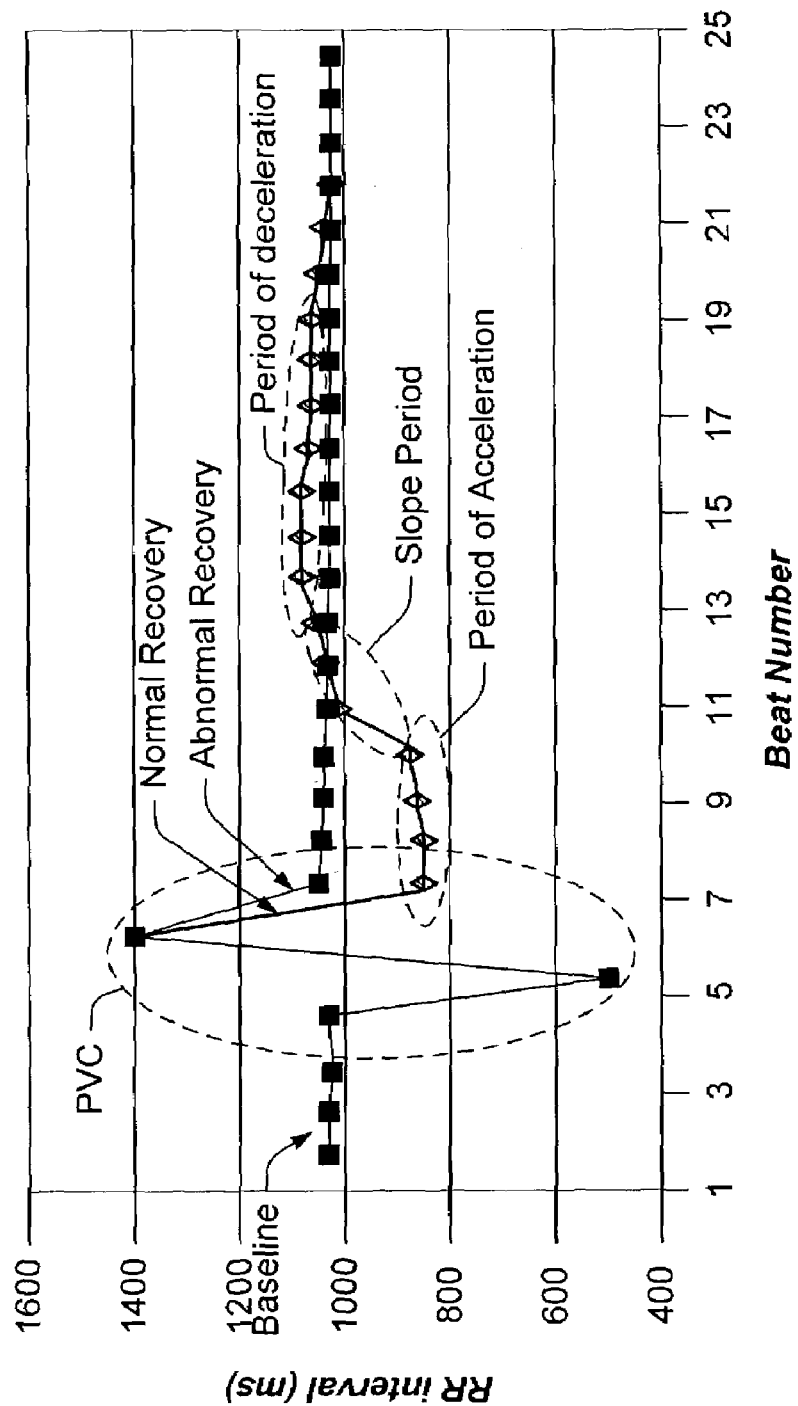
FIG. 4 is a graph that illustrates a PVC and is useful in understanding one or more of the embodiments.

As an example, consider FIG. 4 which shows a graph of RR intervals in ms (y axis) versus beat number (x axis) for a particular patient. Notice first that the patient has an established RR interval baseline which is indicated in the figure just above 1000 ms. A PVC event is indicated in the graph as a spike below the RR interval baseline (corresponding to a very rapid acceleration). This is followed by a spike above the RR interval baseline (corresponding to a rapid deceleration and referred to in the field as a compensatory pause).

In an unhealthy individual or an individual at risk for cardiac problems, the response to a PVC can typically be characterized by a very rapid return to the RR interval baseline. This is indicated in the graph as the "Abnormal Recovery". Notice there, that during or just after the PVC (just after beat 7 or so), the patient's RR interval returns to around the baseline value. Interestingly, this abnormal recovery is similar to the recovery provided by some rate smoothing algorithms.

Figure 5:
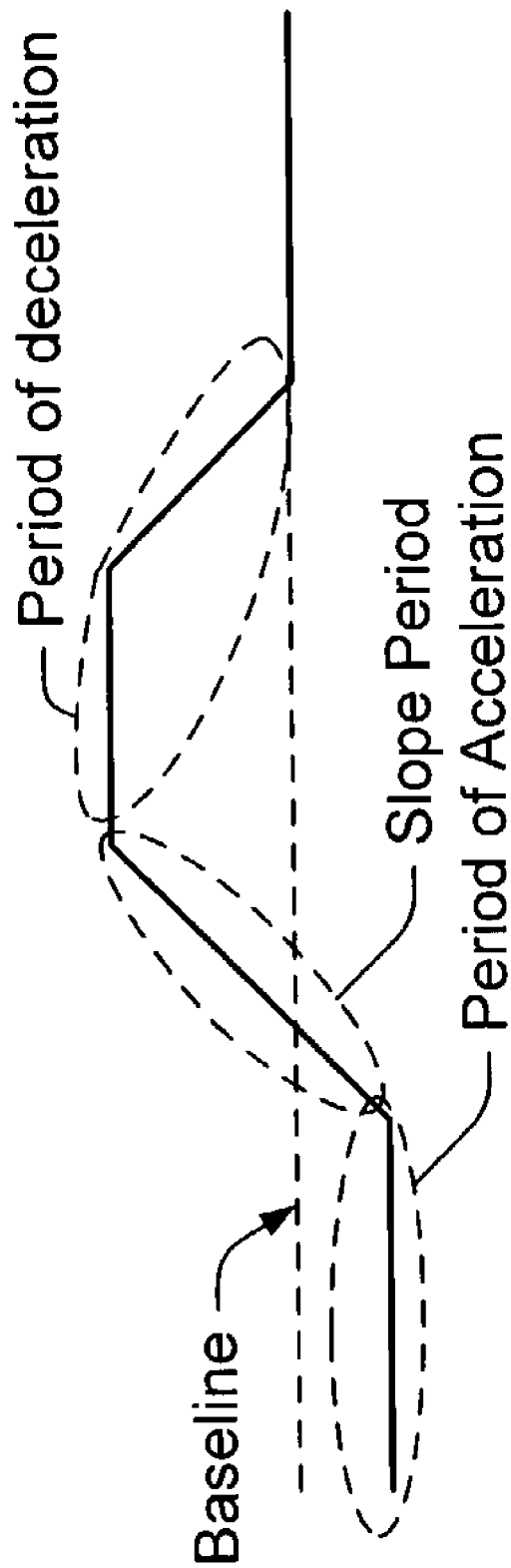
FIG. 5 is an isolated portion of the graph of FIG. 4 and is provided for clarity.

In a healthy individual or an individual who is not presently at risk for cardiac problems, the response is somewhat different. That is, notice on the graph that during a "Normal Recovery" the patient experiences an initial period of heart rate acceleration (characterized by lower values for the RR interval relative to the baseline value), followed by a slope period which, in turn, may be followed by a deceleration period (characterized by higher values for the RR interval relative to the baseline value). After the deceleration period, the patient's RR interval returns to around the baseline RR value. This can be viewed more clearly in FIG. 5 which is an isolated view of the normal recovery relative to the patient's baseline RR value. This period of acceleration and deceleration to below baseline can be considered as a "normal turbulence pattern."

This phenomena has been recognized by others in the field and, most notably, is discussed in an article entitled "Heart-rate turbulence after ventricular premature beats as a predictor of mortality after acute myocardial infarction", authored by Schmidt et al., and appearing in *The Lancet*, Volume 353, Apr. 24, 1999, pages 1390–1396.

Figure 6:
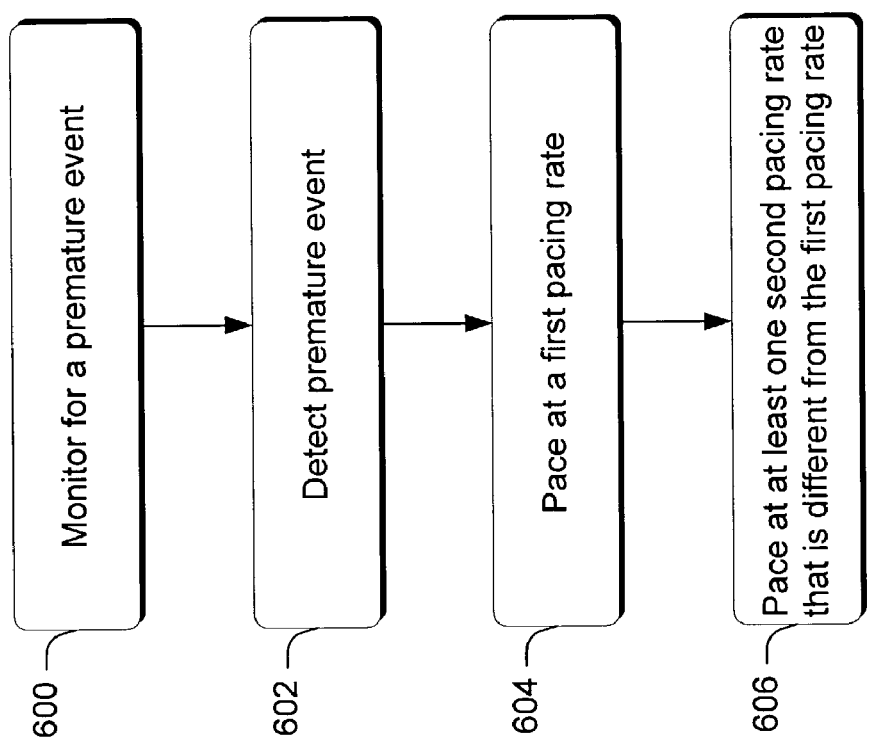
FIG. 6 is a flow diagram that describes steps in a method in accordance with one embodiment.

FIG. 6 is a flow diagram that describes steps in a method in accordance with one embodiment. The steps can be implemented in connection with any suitable hardware, software, firmware or combination thereof. In but one embodiment, the steps can be implemented by a suitably programmed implantable stimulation device. But one example of a stimulation device is given above in FIGS. 1 and 2.

Step 600 monitors for a premature event. The premature event can be any suitable premature event. For example, premature events can comprise atrial or ventricular premature events. Examples of atrial and ventricular premature events include, respectively, premature atrial contractions (PACs) and premature ventricular contractions (PVCs). Step 602 detects a premature event. This step can be implemented using any suitable detection algorithm. Responsive to detecting the premature event, step 604 administers pacing therapy by pacing the patient at a first pacing rate. This step can be implemented by administering multiple pacing pulses at the first pacing rate as defined by an RR interval. This step can be implemented by calculating the first pacing rate based upon the patient's past history. Alternately or additionally, the first pacing rate can be programmed to comprise a pre-determined value or rate that is not specifically a function of the history of the specific patient of interest. Step 606 then administers pacing therapy by pacing the patient at at least one second pacing rate that is different from the first pacing rate. The second pacing rate can be defined in terms of the RR interval. This step can be implemented by calculating the second pacing rate based upon the patient's past history. Alternately or additionally, the second pacing rate can be programmed to comprise a pre-determined value or rate that is not specifically a function of the history of the specific patient of interest. Further, this step can be implemented by pacing at multiple different rates, each of which are different from the first pacing rate. For example, this step can be implemented by using or calculating a transition pacing rate between the first pacing rate and one or more of the second or additional pacing rates. In one example, this transition pacing rate can comprise, for example, a slope period that slopes between the first pacing rate and the second or additional pacing rates. One example of such a slope is given in the examples of FIGS. 4 and 5 above.

In but one embodiment, the second rate (or the multiple different rates following the first pacing rate) can be slower than the first pacing rate. An example of this is given above.

Alternately or additionally, the first pacing rate can be faster than the patient's intrinsic baseline heart rate. The second pacing rate (or the multiple different rates following the first pacing rate) can then be different from this first pacing rate as by, for example, being slower than the first pacing rate.

Alternately or additionally, the second pacing rate can be slower than the patient's intrinsic baseline heart rate. The first pacing rate can then be different from this second rate as by, for example, being faster than the second pacing rate. This first pacing can be, but need not be, faster than the patient's intrinsic baseline heart rate.

Step 606 can further comprise pacing the patient back to a pacing rate that is at or desirably near their intrinsic baseline heart rate.

Together, steps 604 and 606 can be considered as pacing the patient so as to force a turbulence pattern that approximates what is considered to be a normal turbulence pattern in view of the premature event. In the case where the premature event comprises a PVC, this turbulence pattern is defined by an acceleration period followed by a deceleration period with a generally sloped transition therebetween. Of course, with other types of premature events the turbulence patterns can be expected to have different patterns or characteristics.

Specific Premature Ventricular Contraction (PVC) Example

In the example set forth below, the specific example of a PVC with subsequent pacing therapy is described.

Consider the following RR interval sequence:

$R_{-3} R_{-2} R_{-1} R_0 R_1 R_2 R_3 R_4 R_5 R_6$ where the PVC is $R_0$, its coupling interval is $R_0$–$R_{-1}$ and the compensatory pause is the interval $R_1$–$R_0$. The RR intervals can be continuously calculated as is currently performed in many implantable devices such as the one described above. Upon detection of a PVC event ($R_0$), and the occurrence of the first sinus beat after the compensatory pause ($R_1$), pacing therapy can be administered to mimic the physiologically healthy heart recovery from such an event. The first paced beat is $R_2$.

One way of administering pacing therapy so as to mimic the physiologically healthy heart recovery is as follows. First, a couple of parameters should be calculated or otherwise provided. These parameters can be calculated based on a patient's past history. The first of the parameters is known as the "turbulence onset" and is referred to as parameter "$K_1$" in the discussion that follows. Turbulence onset is defined as the difference between the mean of the first two sinus RR intervals after a PVC and the last two sinus RR intervals before the PVC divided by the mean of the last two sinus RR intervals before the PVC. Mathematically speaking, the turbulence onset can be defined as follows:

$$K_1 = \frac{(RR_1 + RR_2) - (RR_{-2} + RR_{-1})}{(RR_{-2} + RR_{-1})} \quad \text{Equation (1)}$$

where $RR_1 = R_2 - R_1$, $RR_2 = R_3 - R_2$, $RR_{-1} = R_{-1} - R_{-2}$, etc.

The second of the parameters is known as the "turbulence slope" and is referred to as parameter "$K_2$" in the discussion that follows. Turbulence slope is defined as the maximum positive slope of a regression line assessed over any sequence of five subsequent sinus-rhythm intervals within the first 20 sinus-rhythm intervals after a PVC. Mathematically speaking, the turbulence slope can be defined as follows:

$K_2 = \max\{\text{slope}(5 \text{ successive } RR \text{ intervals from a window of 20 intervals})\}$     Equation (2)

Using Equations (1) and (2), one can solve for the coupling interval of the first paced beat, which evaluates to:

$RR_1 = \frac{1}{2}[K_1(RR_{-2}+RR_{-1})+(RR_{-2}+RR_{-1})-K_2]$     Equation (3)

Applying Equations (1) and (2), one can also solve for the coupling intervals of the next five beats, which evaluates to:

$RR_N = RR_{N-1} + K_2$, where $N=2, 3$,     Equation (4)

A third parameter, $K_3$, can be introduced and constitutes a delay that can be factored into the pacing scheme. This delay can be utilized to provide a sustained accelerated pacing period (corresponding to the period of acceleration in FIG. 4). That is, as will become apparent below, if the delay parameter is utilized, such can provide the period during which the accelerated pacing takes place. If a non-zero value is used for $K_3$, the parameter $K_2$ is set to zero for a series of 1–15 beats. During the interval that $K_2$ is zero, each paced beat has the same coupling interval as the beat preceding it. The effect is to keep the heart at an elevated rate for a series of beats before the rate is returned to the pre-PVC baseline at a rate determined by $K_2$.

A fourth parameter, $K_4$, can also be introduced and constitutes a delay that can additionally be factored into the pacing scheme. This delay can be utilized to provide a sustained decelerated pacing period (corresponding to the period of deceleration in FIG. 4). If a non-zero value is used for $K_4$, pacing continues at the decelerated rate achieved after N iterations of Equation 4. Pacing continues at this rate for the number of beats determined by $K_4$ or until loss of capture.

Monitoring Mode

Given the above equations and derivations, a device can enter a "monitor mode" in which the various parameters $K_1$, $K_2$, $K_3$, and $K_4$ can be "learned" from a patient's history. Alternately, these parameters can be programmed.

Figure 7:
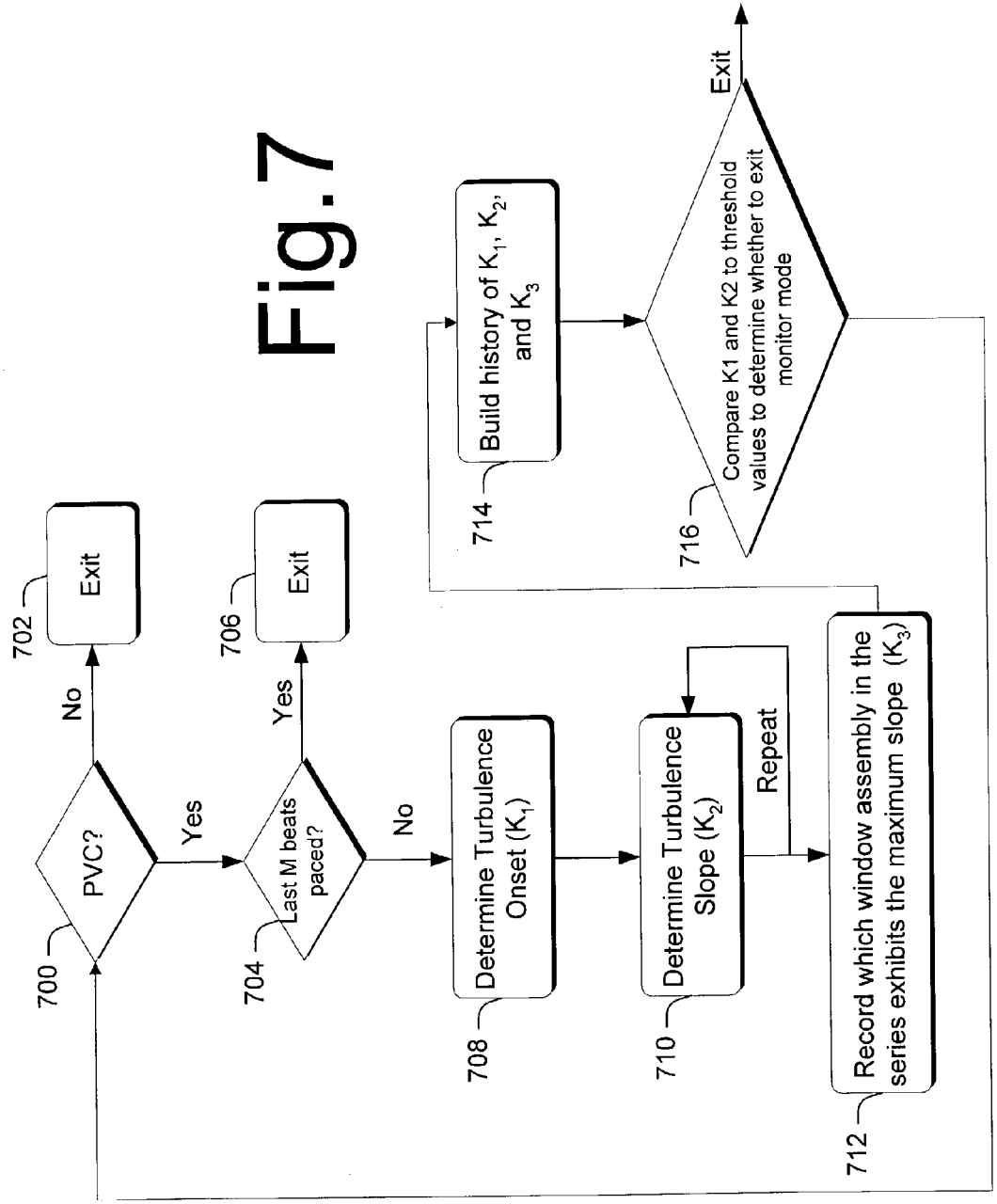
FIG. 7 is a flow diagram that describes steps in a method in accordance with one embodiment.

FIG. 7 is a flow diagram that describes steps in a monitoring mode method in accordance with one embodiment. The steps can be implemented in connection with any suitable hardware, software, firmware or combination thereof. In but one embodiment, the steps can be implemented by a suitably programmed implantable stimulation device. But one example of a stimulation device is given above in FIGS. 1 and 2.

Although not specifically shown in FIG. 7, one step in the monitoring mode method is to monitor a patient for a premature event in the form of a premature ventricular contraction (PVC). Step 700 determines whether a premature event is a PVC. If the event is not a PVC, then step 702 exits the method and continues to monitor the patient. If, on the other hand, the event is a PVC, then step 704 determines whether the last M beats were paced. In this example, M can comprise any suitable number. If the last M beats were paced, then step 706 exits the method and continues to monitor the patient. If, on the other hand, the last M beats were not paced, then step 708 determines the turbulence onset $K_1$. But one way of determining the turbulence onset is by using Equation (1) above. Step 710 determines the turbulence slope $K_2$. But one way of determining the turbulence slope is by using Equation (2) above. In this example, this step is implemented by repeatedly executing Equation (2). Specifically, a sliding window of five RR intervals is advanced through a series of 20 RR intervals. Twenty iterations are used with one value being calculated for each successive sliding window assembly. The turbulence slope is selected to be the maximum of this set of values. If a delay parameter $K_3$ is to be used, step 712 records which window assembly in the series of sliding windows exhibits the maximum slope. If a delay parameter $K_4$ is to be used, step 713 records the duration of the period of decelerated rate. Step 714 then collects and builds the patient's history of $K_1$, $K_2$, $K_3$ and $K_4$ values. Step 716 compares $K_1$ and $K_2$ to threshold values to determine whether to exit the monitor mode due to detected "lack of health". Exemplary nominal thresholds for determining an unhealthy state are the turbulence onset is <0% and for the turbulence slope>2.5 ms/RR. Once the patient is determined to be in a state of compromised health, the algorithm becomes active and delivers pacing pulses following premature events.

Active Mode

Figure 8:
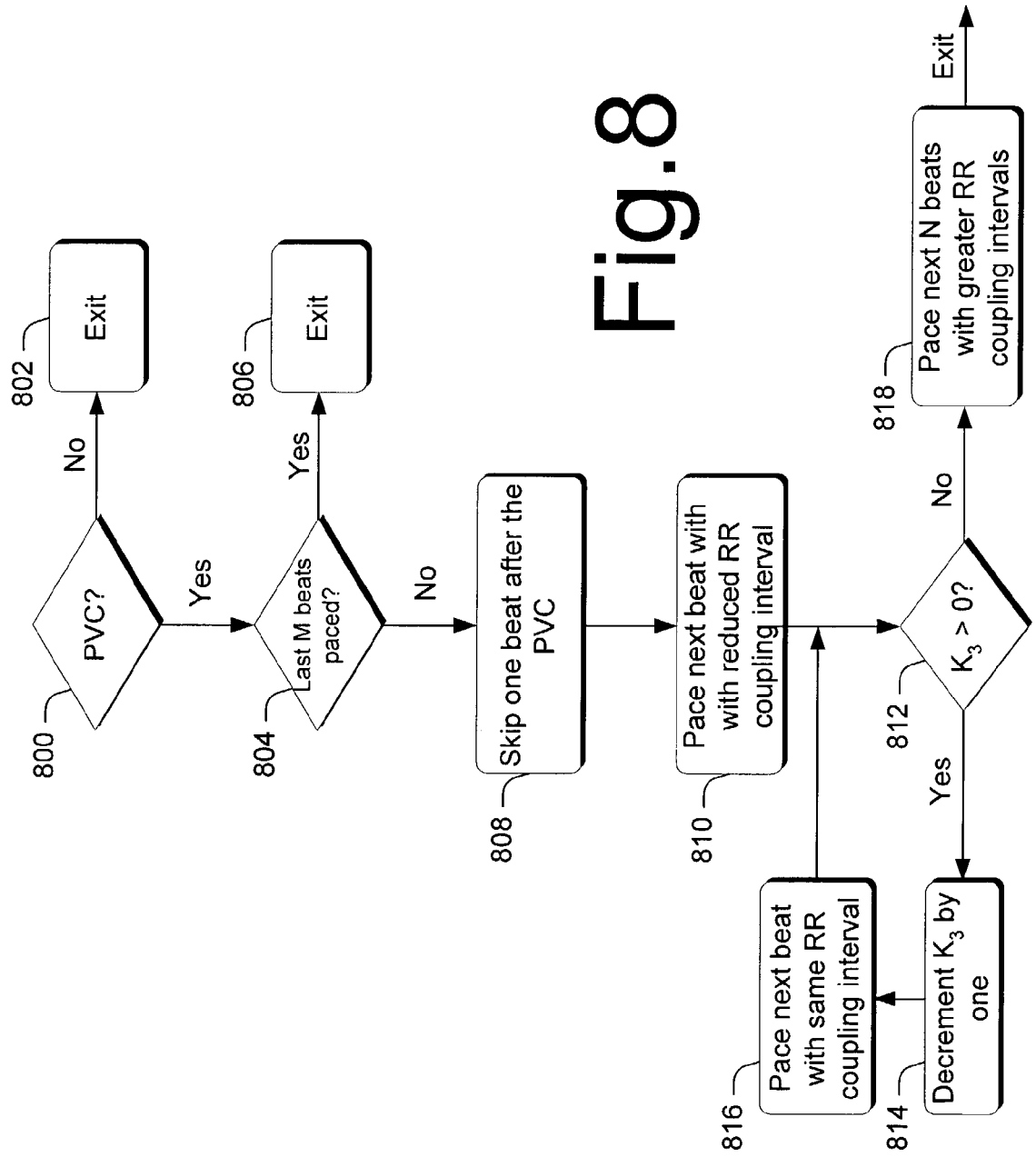
FIG. 8 is a flow diagram that describes steps in a method in accordance with one embodiment.

FIG. 8 is a flow diagram that describes steps in an active mode method in accordance with one embodiment. The steps can be implemented in connection with any suitable hardware, software, firmware or combination thereof. In but one embodiment, the steps can be implemented by a suitably programmed implantable stimulation device. But one example of a stimulation device is given above in FIGS. 1 and 2.

Although not specifically shown in FIG. 8, one step in the active mode method is to monitor a patient for a premature event in the form of a premature ventricular contraction (PVC). Step 800 determines whether a premature event is a PVC. If the event is not a PVC, then step 802 exits the method and continues to monitor the patient. If, on the other hand, the event is a PVC, then step 804 determines whether the last M beats were paced. In this example, M can comprise any suitable number. If the last M beats were paced, then step 806 exits the method and continues to monitor the patient. If, on the other hand, the last M beats were not paced, then step 808 skips one beat after the PVC. Step 810 then paces the next beat using a reduced RR coupling interval. The reduced RR interval is reduced relative to the patient's baseline RR interval and is selected so that the patient can be paced at an accelerated rate. In terms of the FIG. 4 graph, the RR interval is reduced so that the patient can be paced within the area of the graph corresponding to the period of acceleration. One way of calculating the reduced RR interval is set forth above as Equation (3). It should be noted that the parameters $K_1$ and $K_2$ can be computed from the patient's past history as set forth in FIG. 7. Alternately, these parameters can be programmed into the stimulation device. Of course, other methods can be used to calculate the reduced RR interval without departing from the spirit and scope of the claimed subject matter.

Step 812 determines whether $K_3$ is greater than 0. This step is directed to determining the length, if any, that is to be used to pace the patient using the reduced RR interval. In terms of the FIG. 4 graph, this step determines how long the patient is to remain in the period of acceleration. If $K_3$ is greater than 0 (i.e. there is to be some delay), then step 814 decrements $K_3$ by one and step 816 paces the next beat with the same RR interval that was used by step 810 and returns to step 812. This loop is repeated until $K_3$ is no longer greater than 0. When $K_3$ is no longer greater than 0 (indicating the end of the period of acceleration), step 818 paces the next N beats with greater RR intervals. This step is directed to decelerate the pacing rate that is being used to pace the patient. But one way of implementing this step is to use Equation (4) above. In terms of the FIG. 4 graph, this pacing step paces the patient so that their RR intervals correspond to that portion of the graph designated as the slope period. Thus, during this step, the intervals can be gradually increased to decelerate the patient's pacing rate to a point at or below the patient's RR interval baseline value. Subsequently, if the patient is paced to a point below the baseline, the patient can be paced back to base line or pacing can terminate to enable the patient to return to baseline themselves. Additionally, if the patient is paced at a rate below baseline, this may be maintained for a period of deceleration (a plurality of beats) as determined by $K_4$ and as set forth in steps 820–826. Loss of capture during the period of deceleration terminates the pacing algorithm.

CONCLUSION

The various embodiments described above provide a way to reduce the likelihood of arrhythmia onset by effecting a treatment, responsive to a detected premature event, that mimics or otherwise attempts to emulate a healthy heart's natural recovery process. By mimicking or emulating a healthy heart's natural recovery process, it is believed that those conditions that lead to various arrhythmias can be avoided as well, thus reducing the likelihood of a patient experiencing an arrhythmia.

Although the invention has been described in language specific to structural features and/or methodological steps, it is to be understood that the invention defined in the appended claims is not necessarily limited to the specific features or steps described. Rather, the specific features and steps are disclosed as preferred forms of implementing the claimed invention.

What is claimed is:

1. A method comprising:
    monitoring a patient for a premature event associated with a patient's heart;
    detecting a premature event; and
    responsive to detecting the premature event, administering pacing therapy including a period of accelerated pacing faster than the patient's intrinsic heart rate followed by a period of decelerated pacing including pacing slower than the patient's intrinsic heart rate.

2. The method of claim 1, wherein the act of monitoring comprises monitoring for a premature atrial event.

3. The method of claim 1, wherein the act of monitoring comprises monitoring for a premature atrial event in the form of a premature atrial contraction (PAC).

4. The method of claim 1, wherein the act of monitoring comprises monitoring for a premature ventricular event.

5. The method of claim 1, wherein the act of monitoring comprises monitoring for a premature ventricular event in the form of a premature ventricular contraction (PVC).

6. The method of claim 1 further comprising prior to the period of accelerated pacing, calculating an accelerated pacing rate based upon the patient's past history.

7. The method of claim 1, wherein pacing the patient at an accelerated pacing rate comprises pacing the patient at a rate that is not a function of a past history of the patient.

8. The method of claim 1 further comprising prior to the period of decelerated pacing, calculating a decelerated pacing rate based upon the patient's past history.

9. The method of claim 1, wherein the act of pacing the patient at a decelerated pacing rate comprises pacing the patient at a rate that is not a function of a past history of the patient.

10. The method of claim 1, wherein pacing the patient at a decelerated pacing rate comprises pacing at multiple different rates, each of which are slower than the patient's intrinsic heart rate.

11. The method of claim 10, wherein administering pacing further includes pacing the patient at a transition pacing rate between the accelerated pacing rate and at least one of the multiple different decelerated pacing rates.

12. The method of claim 1, wherein the period of decelerated pacing further includes pacing at or near the patient's intrinsic heart rate.

13. The method of claim 1, wherein administering pacing therapy further includes a period of transition pacing at rates between the acceleration period and the deceleration period.

14. A stimulation device comprising:
memory;
one or more processors; and
instructions in the memory which, when executed by the one or more processors, cause the one or more processors to:
  monitor a patient for a premature event associated with a patient's heart;
  detect a premature event; and
  responsive to detecting the premature event, administer pacing therapy including a period of accelerated pacing faster than the patient's intrinsic heart rate followed by a period of decelerated pacing including pacing slower than the patient's intrinsic heart rate.

15. The stimulation device of claim 14, wherein the instructions cause the one or more processors to monitor for a premature atrial event.

16. The stimulation device of claim 14, wherein the instructions cause the one or more processors to monitor for a premature atrial event in the form of a premature atrial contraction (PAC).

17. The stimulation device of claim 14, wherein the instructions cause the one or more processors to monitor for a premature ventricular event.

18. The stimulation device of claim 14, wherein the instructions cause the one or more processors to monitor for a premature ventricular event in the form of a premature ventricular contraction (PVC).

19. The stimulation device of claim 14, wherein the period of decelerated pacing further includes pacing at or near the patient's intrinsic heart rate.

20. The stimulation device of claim 14, wherein the pacing therapy further includes a period of transition pacing at rates between the acceleration period and the deceleration period.

* * * * *